United States Patent [19]
Young et al.

[11] Patent Number: 5,215,741
[45] Date of Patent: Jun. 1, 1993

[54] METHOD FOR PREVENTION OF PARASITE INFECTIONS

[75] Inventors: Alan S. Young, Kikuyu, Kenya; Joseph M. Cummins, Amarillo, Tex.

[73] Assignee: Amarillo Cell Culture Company, Incorporated, Amarillo, Tex.

[21] Appl. No.: 605,687

[22] Filed: Oct. 30, 1990

[51] Int. Cl.$^5$ .............................................. A61K 37/66
[52] U.S. Cl. .................................... 424/85.7; 530/351
[58] Field of Search .................... 424/85.4, 85.5, 85.6, 424/85.7; 530/351

[56]   References Cited
   U.S. PATENT DOCUMENTS

| | | | |
|---|---|---|---|
| 4,915,941 | 4/1990 | Vigouroux | 424/85.4 |
| 5,017,371 | 5/1991 | Cummins | 424/85.4 |

FOREIGN PATENT DOCUMENTS

WO88/03411  5/1988  PCT Int'l Appl. .

OTHER PUBLICATIONS

Kierszenbaum and Sonnenfeld, β-Interferon Inhibits Cell Infection by *T. cruzi*, J. Immunology, vol. 132, No. 2, Feb. 1984.
General Zoology, Sixth Edition, eds. Villee, Walker and Barnes, pp. 452-453.
The Journal of Immunology, vol. 139, pp. 2020-2025, No. 6, Sep. 15, 1987, Louis Schofield et al.
The American Society of Tropical Medicine and Hygiene, 1982, pp. 740-745, Wyler et al.
Parasitology Today, vol. 2, No. 6, 1986, p. 173, J. M. Kelly.
Journal of Interferon Research, 8:251-260, (1988), Badger et al.
J. Parasitol., pp. 194-198, 1982, Kierszenbaum and Sonnenfeld.
The American Journal of Tropical Medicine and Hygiene, vol. 18, No. 6, p. 823, Jaheil et al.
Serono Symp. Publ., (Raven Press), 1985, 24SPRDU, Apr. 20, 1989; Sonnenfeld et al.
International Journal for Parasitology, vol. 18, No. 4, pp. 453-461, 1988, Mutugi et al.
The American Journal of Medicine, May 15, 1984, p. 61, Lowell S. Young, M.D.
Parasitology, (1988), 96, 403-432, A. S. Young, p. 403.
Clin. Exp. Immunol., (1983), 52, 135-143, G. J. Bancroft et al.
Interferon and Nonviral Pathogens, Marcel Dekker, Inc., pp. 217-233, no date, Schofield and Ferreira.

*Primary Examiner*—Jeffrey E. Russel
*Assistant Examiner*—Lynn Touzeau
*Attorney, Agent, or Firm*—Barnes & Thornburg

[57]   ABSTRACT

Development of parasitic infections is Prevented in humans and animals exposed to infective parasitic agents by contacting the oral and pharyngeal mucosa of the human or animal with effective amounts of interferon.

6 Claims, 1 Drawing Sheet

METHOD FOR PREVENTION OF PARASITE INFECTIONS

FIELD OF THE INVENTION

This invention relates to a method for preventing parasite infections. More particularly this invention relates to the use of interferon administered to contact the mucosa of the mouth and throat for treating humans and animal to prevent the development of parasite infections in such hosts exposed to infectious parasitic agents.

BACKGROUND AND SUMMARY OF THE INVENTION

Theileriosis is the most significant disease of livestock in many areas of Africa and is a major obstacle to the development of all forms of the cattle industry on the African continent. East Coast Fever (ECF) is a debilitating and often lethal form of theileriosis caused by the parasite, Theileria parva parva which affects the cattle population in East and Central Africa. ECF has been reported as the cause of half a million cattle deaths per year in East Africa alone. Cattle are infected by ticks carrying t he disease. In an ECF infection, lymphoid cells are first infected and transformed resulting in large infected lymphoblastoid cells which divide regularly to produce two infected daughter cells. This lymphoproliferative phase is followed by a lympodestructive phase when merozoites are liberated from the infected lymphoid cells accompanied by lymphotoxic effects. While the economic losses resulting from ECF mortality are tremendous, additional significant losses may result from reduced productivity, the expense of treatment and control, and the exclusion of more productive breeds of cattle from endemic regions.

Treatment and control measures of both the organism and the tick vector of theileriosis have been difficult due to obstacles presented by the pathogenesis of the disease, contacts between domestic herds, contacts between wild and domestic animals, extensive range areas, cultural and logistic management practices, cost, and geopolitical constraints. While progress has been made in the areas of chemotherapy and immunization, significant problems continue to exist in the control of ECF by these methods.

Parasite infections also afflict man, one of the most common of such infections being malaria, a disease whose treatment still today presents a significant challenge to the medical community.

Several mechanisms of the immune system contribute to anti-parasite host defense. A recent review reported that gamma interferon may be efficacious in the treatment of protozoal infections while alpha or beta interferon has shown little activity. Currently accepted therapeutic treatment regimens for interferon responsive diseases dictate the use of high concentrations of interferon administered intradermally, intravenously, or intramuscularly. However, recent studies using low doses of human alpha interferon and human beta interferon administered orally have shown significant benefits in the stimulation of immunologic variables and in the treatment of diseases of cattle, swine, horses, chickens, cats, dogs and humans.

In accordance with this invention, it has been found that oral treatment with low doses of interferon in a form that Promotes its contact with the oral and pharyngeal mucosa prevents the development of parasitic infections in human and animal hosts exposed to infectious parasites. Effective doses range from about 0.1 to about 10 IU of interferon per kg of host weight. Dosage forms can be solid or semi-solid (gel or paste) or liquid, the solid dosage forms being adapted for dissolving in the host's/patient's mouth.

"Interferon" is a term generically comprehending a group of vertebrate glycoproteins and proteins which are known to have various biological activities, such as antiviral, antiproliferative and immunomodulatory activity, at least in the species of the animal in which such substances are derived. The following definition of "interferon" has been accepted by an international committee assembled to devise a system for the orderly nomenclature of interferons: "To qualify as an interferon a factor must be a protein which exerts virus non-specific, antiviral activity at least in homologous cells through cellular metabolic process involving synthesis of both RNA and protein." *Journal of Interferon Research*, 1, pp. vi (1980). "Interferon" as used herein in describing the present invention shall be deemed to have that definition and shall contemplate proteins, including glycoproteins, regardless of their source or method of preparation or isolation.

Interferons have generally been named in terms of the species of animal cells producing the substance (e.g., human, murine, bovine, etc.), the type of cell involved (e.g., leukocyte, lymphoblastoid, fibroblast) and, occasionally, the type of inducing material responsible for the interferon production (e.g., virus, immune). Interferon has been loosely classified by some researchers according to the induction mode as either Type I or Type II, with the former classification comprehending viral and nucleic acid induced interferon, and the latter class including the material produced as a lymphokine through induction by antigens and mitogens. More recently, an orderly nomenclature system for interferon has been devised which classifies interferons into types on the basis of antigenic specificities. Under this newer classification system, the designations alpha, beta and gamma have been used to correspond to previous designations of leukocyte, fibroblast and Type II (immune) interferons, respectively. Alpha and beta interferons are usually acid-stable and correspond to what have been called Type I interferons. Gamma interferons are usually acid-labile and correspond to what have been called Type II interferons.

The use of interferon for the treatment of disease in man and animals has been the subject of intense ongoing research efforts in many laboratories, both in industry and in educational institutions around the world. In some of the earliest research activities interferon was shown to have antiviral properties and the most successful clinical therapeutical applications to date have been in the treatment of virus-related disease states. More recently it has been found that exogenous interferon is effective for the regression or remission of some metastatic disease states. The literature is replete with reports of research and development efforts directed to defining activities and potential therapeutic uses of interferon. Most of the reports described activities of interferon in vitro or its effects in vivo following parenteral, particularly intramuscular and intradermal administration. There have been some reports of successful topical and intranasal usages. It has seldom been administered intravenously because of substantial adverse effects attributable to "contaminants" in crude and even highly purified isolates. While the advent of recombinant DNA technology has allowed production of pure interferon species, intravenous administration of such pure compositions are not without adverse effects. The Food and Drug Administration has approved the use of alpha-interferon administered parenterally in high doses for the treatment of human hairy cell leukemia and for several other indications.

Before the first report of a successful oral administration of interferon in now issued U.S. Pat. No. 4,462,985, there was no recognition in the art of the potential offered by oral administration of interferon. The generally held belief was that interferon could not survive the digestive conditions of the alimentary canal. Since the first disclosure of the immunotherapeutic benefit achieved via oral administration of interferon, we have continued to investigate the efficacy of orally administered interferon. U.S. Pat. No. 4,497,795, issued Feb. 5 1985, describes and claims the use of interferon administered orally or via intravenous administration to stimulate appetite and feed efficiency of animal species. U.S. patents have also issued for the use of interferon at dosages less than about 5 IU/lb of body weight for increasing feed efficiency and food utilization in warmblooded vertebrates, for preventing and treating shipping fever, and for enhancing vaccine efficiency. More recently, it was discovered that the efficacy of orally administered interferon can be realized simply by administering it in a form which promotes contact of the interferon dosage with the mucosal lining of the mouth and throat.

DETAILED DESCRIPTION OF THE INVENTION

Figure 1:
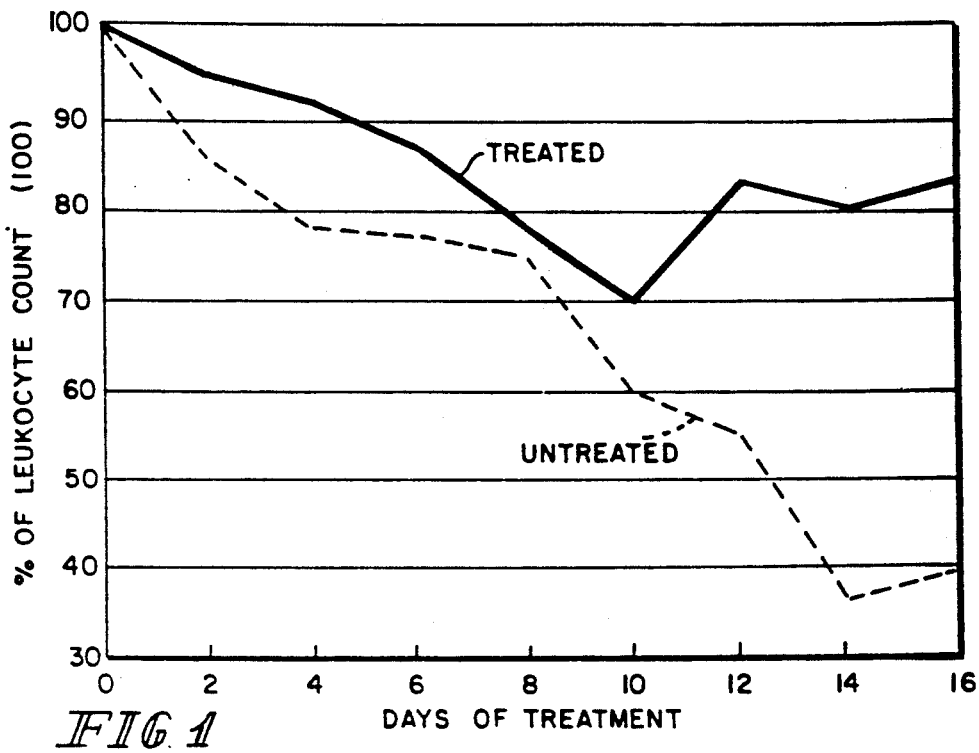
FIG. 1 is a graph showing relative changes in peripheral blood leukocyte count in IFN treated and untreated bulls inoculated at day 0 with T. parva parva.

In accordance with one preferred embodiment of the present invention, the development and progression of a parasite infection in a host having exposure to an infective parasite agent is prevented by a method comprising contacting the oral and pharyngeal mucosa of said host with a therapeutically effective amount of interferon.

The interferon administered can be derived from human or animal cell culture, and in accordance with the preferred embodiments is alpha or beta interferon. Interferons useful in accordance with this invention can also be isolated from microorganisms produced by recombinant engineering techniques to contain one or more functioning genes for human or animal interferon. Proteins having activities similar to natural occurring interferons but with modified amino acid sequences are also contemplated as useful in accordance with this invention. The clinical agents of choice for use in the present invention is human leukocyte interferon or lymphoblastoid interferon, mass produced by procedures involving collection and purification of quantities of human buffycoat leukocytes or lymphoblastoid cells, induction of interferon production, and isolation of interferon from culture media.

Interferon of human and murine origin has been quantified in the art in terms of International Units ("IU"). Interferons of other than human or murine origin can be used in accordance with this invention, and to the extent that application of "International Units" to those interferons may be outside presently accepted Practices for specification of quantities of said interferons, it shall be understood that amounts of non-human interferons having the same efficacy as the quantities (IU's) of human interferon specified in accordance with this description is within the scope of the present invention.

Effective dosage levels of oral interferon for use in accordance with this invention are low compared to levels of interferon commonly accepted as appropriate for parenteral administration for treatment of human and animal diseases. Recent human therapeutic indications, clinical trials and experimental studies have used Parenteral doses of interferon in the range of millions of IU per day. In accordance with this invention interferon is administered for contact with the oral and pharyngeal mucosa at a preferred dosage level of about 0.1 to about 10 IU/kg of host body weight per day and more preferably about 0.1 to about 5.0 IU/kg of host body weight per day. Preferred interferons for use in this method are alpha and beta interferons of human or non-human species origin. Interferons produced by leukocytes or lymphoblastoid cells are most preferred.

Interferon is administered to the host in a dosage form adapted to promote contact with the administered interferon with the host's oral and Pharyngeal mucosa. Oral Interferon can be administered in accordance with this invention in either a liquid (solution) or in solid dosage form. Thus interferon can be administered in a buffered aqueous solution typically containing a stabilizing amount (1-5% by weight) of albumin or blood serum. Exemplary of a buffered solution suitable as a carrier of interferon administered in accordance with this invention is a phosphate buffered saline solution prepared as follows: A concentrated (20×) solution of phosphate buffered saline (PBS) is prepared by dissolving the following reagents in sufficient water to make 1000 ml of solution: sodium chloride, 160 g.; potassium chloride 4.0 g.; sodium hydrogen phosphate 23 g.; potassium dihydrogen phosphate 4.0 g.; and optionally, phenol red powder 0.4g. The solution is sterilized by autoclaving at 15 lbs. pressure for 15 minutes and then diluted with additional water to a single strength concentration prior to use.

Alternatively the interferon utilized in accordance with this invention can be formulated into flavored or unflavored solutions or syrups, for example, using a buffered aqueous solution of interferon as a base with added excipients such as caloric or non-caloric sweeteners, flavors, humectants, and other pharmaceutically acceptable excipients.

A solid dosage form, such as a powder or a lozenge adapted to be dissolved upon contact with saliva in the mouth, with or without the assistance of chewing is an equally acceptable means for administering interferon to humans in accordance with this invention. Such a unitary dosage form is preferably formulated to release about 1 to about 1500 IU of interferon upon dissolution in the mouth for contact with the oral and pharyngeal mucosa. Thus a unitary dosage form of interferon for use in accordance with this invention can be prepared by art-recognized techniques for forming compressed tablets such as chewable vitamins. Similarly, interferon can be incorporated, for example, into a starch-based gel formulation which will dissolve and release interferon for contact with the oral mucosa when held in the mouth. Solid unitary dosage forms of interferon for use in accordance with this present invention can be prepared utilizing art-recognized dose formulation techniques. The pH of such formulations can range from about 4 to about 8.5.

Liquid (solution or suspension) dosage forms can be used efficiently on both human and animal species Solid unit dosage forms are particularly suited for human administration, where the patient can be instructed not to swallow the unit dose form, but instead hold it in the mouth until it dissolves. Solid dosage forms suitable for administration of interferon to animals in accordance with this invention includes interferon containing powder or granules or interferon-containing salt or molasses blocks which are licked by animals having access thereto.

Oral Interferon administered in accordance with this invention has been found effective for preventing the development of East Coast Fever in cattle exposed to *Theileria parva parva*.

Preparation of Human Alpha-Interferon

Human alpha-interferon can be prepared through the following procedure, commonly referred to as the Cantell procedure. The process begins with packs of human leukocytes. The buffy coats in these packs are pooled into centrifuge bottles, and then are diluted with 0.83% ammonium chloride. The mixture is incubated for 15 minutes with intermittent shaking, and is then centrifuged for 20 minutes at 2000 rpm. The supernatant is discarded, and the cell pellets are resuspended with a minimal volume of sterile PBS. The mixture is then diluted with ammonium chloride and centrifuged. The supernatant is again discarded, and the remaining cell pellets are resuspended with a minimal volume of a tissue culture medium such as Minimal Essential Medium (MEM), available from KC Biological. The cell concentration is determined with a Coulter counter.

Interferon induction takes place in glass or plastic bottles. The induction medium contains MEM, 75mM Hepes (available from Calbiochem), 75mM Tricine (available from Sigma Chemical Co.), human agamma serum (18mg/ml), and gentamycin sulfate (from M.A. Bioproducts; 50mcg/ml). The cells are added to the induction vessels at a final concentration of about 5 to 10 million cells per milliliter. The induction vessel is incubated in a 37° C. water bath, and alpha-interferon is added as a primer.

After two hours, Sendai virus is added to the induction mixture. This causes alpha interferon to be produced in the supernatant by the leukocytes. After a 12-18 hour incubation time, the induction mixture is centrifuged. The cells are discarded, and the supernatant is then purified.

The crude interferon is chilled to 10° C. or below in an ice bath. Five molar potassium thiocyanate is added to obtain a final concentration of 0.5M. This solution is stirred for 15 minutes, and then its pH is lowered to 3.3 by adding hydrochloric acid. The mixture is then centrifuged at 2800 rpm for 30 minutes, and the supernatant is discarded.

The pellets are then resuspended in 95% ethanol and are stirred for 15 minutes. This suspension is centrifuged at 2800 rpm for 20 minutes, and the pellets are discarded. The pH of the supernatant is then adjusted to 5.8 with sodium hydroxide. The mixture is stirred for 10 minutes, and then centrifuged at 2800 rpm for 20 minutes. The pellets are discarded. The pH of the supernatant is then adjusted to 8 with sodium hydroxide. This solution is stirred for 10 minutes, followed by centrifugation at 2800 rpm for 20 minutes. The supernatant is discarded, and the pellets are resuspended with 0.5M potassium thiocyanate in a 0.1M sodium phosphate buffer. This suspension is stirred at 4° C.

Next, the suspension is centrifuged at 2800 rpm for 20 minutes, and the pellets are discarded. The pH of the supernatant is adjusted to 5.3 with hydrochloric acid. After stirring for 10 minutes and centrifugation, the pH of the supernatant is adjusted to 2.8 with hydrochloric acid, followed by further stirring for 20 minutes. This mixture is centrifuged at 2800 rpm, and the resulting pellet is purified human alpha-interferon.

The pellet is resuspended with 0.5M potassium thiocyanate in 0.1M sodium phosphate buffer, having a pH of 8.0. It is then dialyzed against PBS at 4° C., with two changes of PBS. This mixture is then centrifuged and the precipitate is discarded. The remaining purified alpha interferon is sterilized by filtration through a 0.2 micron filter.

Other procedures are, of course, available for making interferons. For example, U.S. Pat. No. 4,376,821 and 4,460,685 disclose methods of making human gamma-interferon, U.S. Pat. No. 4,276,282 discloses methods of making lymphoblastoid interferon. A method of making bovine fibroblast (beta) interferon is disclosed in applicant's U.S. Pat. No. 4,462,985. Interferon Preparations are commercially available from Hoffmann-RaRoche, Burroughs-Wellcome and Schering-Plough.

EXAMPLE 1

Eight Friesian bulls were weighed and randomly assigned to 1 of 2 treatment groups. The bulls were inoculated, by subcutaneous injection, (day 0) with a $10^{-1}$ dilution of a sporozoite stabilate of *T.p. parva* (Marikebuni) stock (St IL 3014). Four of the cattle were treated daily with an oral liquid dosage containing 1 international unit/kg body weight (IU/kg bwt) of human alpha-interferon (prepared by method of Cantell) from day (d) −2 to +8. Needle biopsies were taken from parotid lymph nodes starting at d +5, smears prepared, stained with Giemsa's stain and examined for the presence of theilerial schizonts. Starting at d +10 biopsies were collected from the contra-lateral prescapular lymph nodes. Bulls were bled at regular intervals to determine haematocrit, haemoglobin (hemoglobinometer, Coulter Electronics, Inc., Florida, USA), erythrocyte and total leukocyte values (model ZB2 Coulter Counter, Coulter Electronics). Bulls were bled on d +28 and +35 and the sera assayed for the presence of antibody to *T. p. parva* schizont antigen by indirect florescent antibody test. On d +42, surviving bulls were reinoculated with 1 ml of undiluted homologous stabilate and considered immune if they survived this second inoculation. Rectal temperatures of calves were taken daily. A temperature >39.5° C. and the presence of theilerial parasitosis in the lymph nodes was considered diagnostic for clinical disease. Complete post mortem examinations were performed on all dead bulls to determine the cause of death.

None of the 4 bulls given interferon developed clinical theileriosis and patent schizont parasitosis was observed in 2 animals for a total of 2 d. In contrast, 3 of the 4 untreated control bulls died of theileriosis while the fourth had a only parasitosis. Untreated cattle had a group total of 32 d of parasitosis and 15 d of fever. An average reduction from initial total white blood cell concentrations of 17% and 60% was observed in both treated and control groups, respectively. Three of 4 treated bulls and the one surviving control bull developed a detectable antibody response to T.p. parva schizont antigen. On d +42, all surviving bulls were reinoculated with a 10 fold higher does of stabilate. The one surviving control animal and 1 of the 4 treated bulls survived the second stabilate inoculation (see Table 1).

Since the destruction of lymphoid cells is characteristic of ECF, an examination of the percent change in the number of leukocytes present in the animal's blood is an indication of the severity of the infection. As is shown in FIG. 1 initially the leukocyte population of both interferon treated cattle (solid line) and untreated cattle (dashed line) declined. However, in the interferon treated cattle the leukocyte population stablized at approximately d 12 whereas the untreated cattle's leukocyte population continued to decline up to d 18. Day 18 is the time when 2 of the 4 untreated cattle died.

fied Cantell procedure and then subjected to further purification using immobilized monoclonal antibody affinity chromatography. Three of the groups of bulls were treated orally once daily with either 1 IU human alpha-interferon (Cantell), 1 IU human alpha-interferon (ISI), or 10 IU human alpha-interferon (ISI)/kg bwt from day (d) −2 to d +8. As in Example 1, all animals in a treatment group were given human alpha-interferon orally once each day from d −2 to +8. On d 0 all bulls were inoculated with a $10^{-1}$ dilution of St IL 3014 and monitored in a manner similar to Example 1 with the exception that the bulls were bled for sera weekly, and were reinoculated with undiluted stabilate on day +35.

Of the calves which developed clinically defined theileriosis, 2 of 2 control bulls, 1 of 2 bulls given 10 IU human alpha-interferon (ISI), and 0 of 1 bull given 1 IU human alpha-interferon (ISI), died. None of the animals

TABLE 1

Reaction of calves treated with interferon inoculated with *Theileria parva parva* (Marikebuni) stabilate IL 3014 compared to untreated control calves.

| Group | Cattle No. | Days after infection to | | | | Reciprocal IFAT titre on day 35 after infection | Reinoculation[1] |
|---|---|---|---|---|---|---|---|
| | | Schizonts | Fever | Recovery | Death | | |
| Untreated | 503 | 10 | 13 | — | 21 | — | — |
| | 504 | 14 | — | 18 | — | 160 | I |
| | 505 | 11 | 14 | — | 18 | — | — |
| | 507 | 11 | 14 | — | 18 | — | — |
| | Mean | 11.5 | 13.7 | 18 | 19.0 | | |
| | Total days of | 32 | 15 | — | — | | |
| Treated | 506 | 13 | — | 14 | — | — | I |
| | 508 | — | — | — | — | <40 | NI |
| | 509 | — | — | — | — | 40 | NI |
| | 510 | 11 | — | 12 | — | 640 | NI |
| | Mean | 12.0 | 0/4 | 13.0 | 0/4 | | |
| | Total days of | 2 | 0 | — | — | | |

[1] I = Immune and lived after reinoculation. NI = not immune after reinoculation and died.

EXAMPLE 2

Sixteen Friesian bulls were weighed and randomly divided into 4 groups of 4 and inoculated with *T.p. parva* as described in Example 1. Two different preparations of human interferon were used in treating the bulls. Human alpha-interferon (Cantell) was prepared/isolated by the Cantell procedure as described above. Human alpha-interferon (ISI) was prepared by a modiin the 1 IU human alpha-interferon (Cantell) treatment group developed theileriosis. Total group days of parasitosis/fever for the control, 10 IU (ISI), 1 IU (ISI) and 1 IU (Cantell) groups were 30/7, 17/6, 9/3 and 5/0, respectively. All surviving cattle were immune to subsequent reinoculation with a 10-fold higher dose of homologous stabilate, except 1 bull from the 10 IU (ISI) and 1 from the 1 IU (ISI) groups (see Table 2).

TABLE 2

Reaction of calves treated with interferon inoculated with *Theileria parva parva* (Marikebuni) stabilate IL 3014 compared to untreated control calves.

| Group | Cattle No. | Days after infection to | | | | Reciprocal IFAT titre on day 35 after infection | Reinoculation[1] |
|---|---|---|---|---|---|---|---|
| | | Schizonts | Fever | Recovery | Death | | |
| Untreated | 792 | 11 | — | 19 | — | 10,240 | I |
| | 793 | 10 | 16 | — | 17 | — | — |
| | 794 | 11 | — | 16 | — | 2,560 | I |
| | 795 | 10 | 13 | — | 18 | — | — |
| | Mean | 10.5 | 14.5 | 17.5 | 17.5 | | |
| | Total days of | 30 | 7 | — | — | | |
| 10 IU/kg HuIFN-a (ISI) | 796 | — | — | — | — | 10,240 | I |
| | 797 | 12 | 15 | — | 22 | — | — |
| | 798 | — | — | — | — | 40 | NI |
| | 799 | 10 | 15 | 19 | — | 10,240 | I |
| | Mean | 11.0 | 15.0 | 19 | 22 | | |
| | Total days of | 17 | 6 | — | — | | |
| 1 IU/kg HuIFN-a (ISI) | 803 | — | — | — | — | 40 | NI |
| | 801 | 8 | — | 12 | — | 2,560 | I |
| | 800 | 11 | — | 12 | — | — | ND[2] |
| | 804 | 13 | 15 | 21 | — | 10,240 | I |
| | Mean | 10.7 | 15 | 15.0 | 0/4 | | |
| | Total days of | 9 | 3 | — | — | | |
| 1 IU/kg HuIFN-a | 805 | — | — | — | — | 2,560 | I |
| | 806 | 11 | — | 16 | — | 10,240 | ND |

TABLE 2-continued

Reaction of calves treated with interferon inoculated with *Theileria parva parva* (Marikebuni) stabilate IL 3014 compared to untreated control calves.

| Group | Cattle No. | Days after infection to | | | | Reciprocal IFAT titre on day 35 after infection | Reinoculation[1] |
|---|---|---|---|---|---|---|---|
| | | Schizonts | Fever | Recovery | Death | | |
| (Cantell) | 807 | 11 | — | 12 | — | 2,500 | I |
| | 809 | — | — | — | — | 640 | I |
| | Total days of | 5 | 0 | — | — | | |

[1] I = immune and lived after reinoculation. NI = not immune after reinoculation and died.
[2] Not determined.

Figure 2:
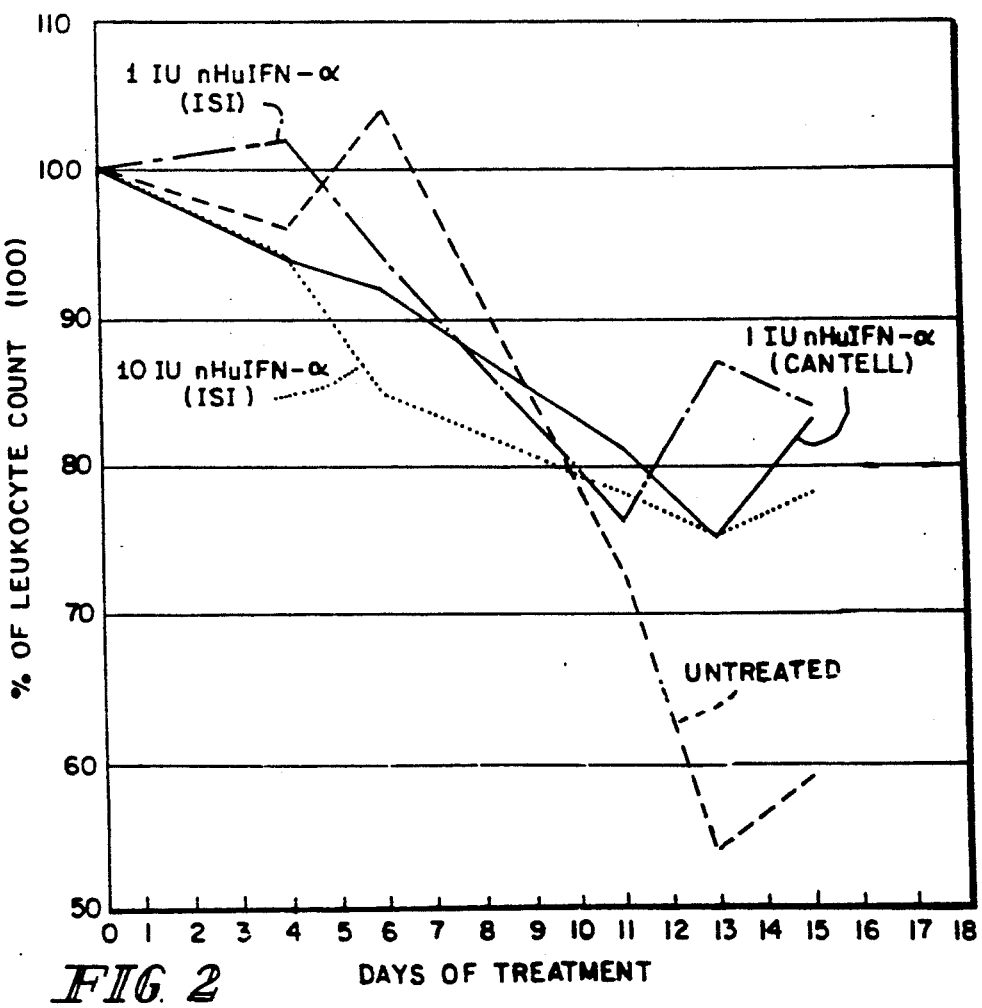
FIG. 2 is a graph similar to FIG. 1 summarizing data from three treatment groups and one control group.

The number of leukocytes present in the blood of the infected animals is shown in FIG. 2. Relative mean percentage changes in peripheral blood leukocyte counts of bulls inoculated (day 0) with a *T. parva parva* stabilate. Again, each group consisted of 4 bulls treated once daily (day −2 to day +8) with either 10 IU nHuIFN-a (ISI: dotted line), 1 IU nHuIFN-a (ISI; broken line), 1 IU nHuIFN-a (Cantell) /kg body weight (solid line), and untreated control group (dashed line). After an initial decline in leukocyte number, the leukocyte population stablizes in interferon treated cattle at approximately d 11. However, in untreated cattle the leukocyte population continued to decline out to d 16.

We claim:

1. A method for treating a human or animal exposed to an infective parasitic agent, said method comprising the step of contacting the oral and pharyngeal mucosa of said human or animal with alpha interferon in an amount effective to prevent development of a parasite infection.

2. The method of claim 1 wherein the interferon is alpha-interferon administered daily during treatment.

3. The method of claim 1 wherein the interferon is human leukocyte interferon.

4. The method of claim 1 wherein the interferon is administered to a human in a dosage form adapted to be held in the mouth for a period of time to maximize contact of the interferon with the oral and pharyngeal mucosa.

5. The method of claim 1 wherein about 0.1 to about 10 IU of interferon per kg of body weight is administered.

6. The method of claim 5 wherein the interferon is produced from leukocytes or lymphoblastoid cells.

* * * * *